(12) United States Patent
Beyar et al.

(10) Patent No.: US 8,600,477 B2
(45) Date of Patent: Dec. 3, 2013

(54) IMAGE-GUIDED NAVIGATION FOR CATHETER-BASED INTERVENTIONS

(75) Inventors: Rafael Beyar, Haifa (IL); Tal Wenderow, Haifa (IL)

(73) Assignee: Corindus, Inc., Waltham, MA (US)

( * ) Notice: Subject to any disclaimer, the term of this patent is extended or adjusted under 35 U.S.C. 154(b) by 564 days.

(21) Appl. No.: 11/660,320

(22) PCT Filed: Aug. 16, 2005

(86) PCT No.: PCT/IL2005/000887
§ 371 (c)(1),
(2), (4) Date: Jul. 26, 2007

(87) PCT Pub. No.: WO2006/018841
PCT Pub. Date: Feb. 23, 2006

(65) Prior Publication Data
US 2007/0276216 A1    Nov. 29, 2007

Related U.S. Application Data

(60) Provisional application No. 60/601,629, filed on Aug. 16, 2004.

(51) Int. Cl.
*A61B 5/00*    (2006.01)

(52) U.S. Cl.
USPC ............ 600/424; 600/427; 600/428; 128/899

(58) Field of Classification Search
USPC .......... 600/407, 424, 425, 427, 429; 128/899
See application file for complete search history.

(56) References Cited

U.S. PATENT DOCUMENTS

| | | | |
|---|---|---|---|
| 2,718,598 A | 9/1955 | Graf | |
| 3,147,953 A | 9/1964 | Arth | |
| 3,308,297 A | 3/1967 | Mansker | |
| 4,254,341 A | 3/1981 | Herr et al. | |
| 4,382,184 A * | 5/1983 | Wernikoff | ........................ 378/37 |

(Continued)

FOREIGN PATENT DOCUMENTS

| | | |
|---|---|---|
| EP | 0 329 492 A2 | 8/1989 |
| EP | 0 331 944 A1 | 9/1989 |

(Continued)

OTHER PUBLICATIONS

Extended European Search report for European Patent Application No. 05764607.7-1265, mailed Jul. 21, 2009, 9 pages.

(Continued)

*Primary Examiner* — Ruth S Smith
(74) *Attorney, Agent, or Firm* — Rathe Lindenbaum LLP (57) ABSTRACT

A navigation system for catheter-based interventions, the system comprising a processing device; an angiogram x-ray system connected by data transfer connection to the processing device and capable of capturing angiographic images of a patient; an electrocardiogram monitoring device that is also connected by data transfer connection to the processing device and to the x-ray system; a medical instrument to be inserted into the area of the patient captured by the angiographic image; a position capture module for getting position information about the position of the medical instrument, the unit connected by data transfer connection to the processing device, wherein the processing device is capable of triggering the capturing of the angiographic images as a roadmap and superimposing on the roadmap the position information about the medical instrument.

18 Claims, 3 Drawing Sheets

(56) References Cited

U.S. PATENT DOCUMENTS

| | | | |
|---|---|---|---|
| 4,581,538 A | 4/1986 | Lenhart | |
| 4,965,456 A | 10/1990 | Huettenrauch et al. | |
| 4,977,588 A | 12/1990 | Van der Ende | |
| 5,049,147 A | 9/1991 | Danon | |
| 5,090,044 A | 2/1992 | Kobayashi | |
| 5,139,473 A | 8/1992 | Bradshaw et al. | |
| 5,185,778 A | 2/1993 | Magram | |
| 5,377,678 A | 1/1995 | Dumoulin et al. | |
| 5,425,382 A * | 6/1995 | Golden et al. | 128/899 |
| 5,434,775 A | 7/1995 | Sims et al. | |
| 5,464,023 A | 11/1995 | Viera | |
| 5,487,734 A | 1/1996 | Thorne et al. | |
| 5,492,131 A | 2/1996 | Galel | |
| 5,578,014 A | 11/1996 | Erez et al. | |
| 5,584,078 A | 12/1996 | Saboory | |
| 5,623,943 A | 4/1997 | Hackett et al. | |
| 5,644,613 A * | 7/1997 | Mick | 378/98.12 |
| 5,654,864 A | 8/1997 | Ritter et al. | |
| 5,690,645 A | 11/1997 | Van Erp | |
| 5,706,827 A | 1/1998 | Ehr et al. | |
| 5,821,920 A | 10/1998 | Rosenberg et al. | |
| 5,842,987 A | 12/1998 | Sahadevan | |
| 5,851,182 A | 12/1998 | Sahadevan | |
| 5,882,333 A | 3/1999 | Schaer et al. | |
| 5,957,941 A | 9/1999 | Ream | |
| 5,981,964 A | 11/1999 | McAuley et al. | |
| 6,004,276 A | 12/1999 | Wright et al. | |
| 6,013,038 A | 1/2000 | Pflueger | |
| 6,048,300 A | 4/2000 | Thornton et al. | |
| 6,083,170 A | 7/2000 | Ben-Haim | |
| 6,096,004 A | 8/2000 | Meglan et al. | |
| 6,126,647 A | 10/2000 | Posey et al. | |
| 6,171,234 B1 | 1/2001 | White et al. | |
| 6,233,476 B1 | 5/2001 | Strommer et al. | |
| 6,266,552 B1 * | 7/2001 | Slettenmark | 600/424 |
| 6,285,898 B1 | 9/2001 | Ben-Haim | |
| 6,351,513 B1 * | 2/2002 | Bani-Hashemi et al. | 378/8 |
| 6,375,471 B1 | 4/2002 | Wendlandt et al. | |
| 6,447,504 B1 | 9/2002 | Ben-Haim et al. | |
| 6,499,163 B1 | 12/2002 | Stensby | |
| 6,554,472 B1 | 4/2003 | Dietz et al. | |
| 6,705,990 B1 | 3/2004 | Gallant et al. | |
| 6,726,675 B1 | 4/2004 | Beyar | |
| 6,740,103 B2 | 5/2004 | Hall et al. | |
| 6,770,066 B1 | 8/2004 | Weaver et al. | |
| 6,834,201 B2 | 12/2004 | Gillies et al. | |
| 6,878,106 B1 | 4/2005 | Herrmann | |
| 7,112,811 B2 | 9/2006 | Lemer | |
| 7,276,044 B2 | 10/2007 | Ferry et al. | |
| 7,608,847 B2 | 10/2009 | Rees | |
| 7,615,042 B2 | 11/2009 | Beyar et al. | |
| 7,697,972 B2 * | 4/2010 | Verard et al. | 600/424 |
| D626,250 S | 10/2010 | Wenderow et al. | |
| 7,887,549 B2 | 2/2011 | Wenderow et al. | |
| 2001/0025142 A1 | 9/2001 | Wessels et al. | |
| 2002/0109107 A1 | 8/2002 | Goldstein | |
| 2002/0115931 A1 * | 8/2002 | Strauss et al. | 600/420 |
| 2002/0168618 A1 | 11/2002 | Anderson et al. | |
| 2002/0177789 A1 | 11/2002 | Ferry et al. | |
| 2003/0040671 A1 | 2/2003 | Somogyi et al. | |
| 2003/0069719 A1 | 4/2003 | Cunningham et al. | |
| 2003/0078003 A1 | 4/2003 | Hunter et al. | |
| 2003/0088209 A1 | 5/2003 | Chiu et al. | |
| 2003/0176770 A1 | 9/2003 | Merril et al. | |
| 2003/0199848 A1 | 10/2003 | Ledesma et al. | |
| 2004/0044279 A1 | 3/2004 | Lewin et al. | |
| 2004/0064086 A1 | 4/2004 | Gottlieb et al. | |
| 2004/0068173 A1 | 4/2004 | Viswanathan | |
| 2004/0113498 A1 | 6/2004 | Kroenke | |
| 2004/0138548 A1 * | 7/2004 | Strommer et al. | 600/407 |
| 2004/0152974 A1 | 8/2004 | Solomon | |
| 2004/0254566 A1 | 12/2004 | Plicchi et al. | |
| 2005/0008210 A1 | 1/2005 | Evron et al. | |
| 2005/0222554 A1 | 10/2005 | Wallace et al. | |
| 2005/0245846 A1 | 11/2005 | Casey | |
| 2005/0256504 A1 | 11/2005 | Long et al. | |
| 2005/0277851 A1 | 12/2005 | Whittaker et al. | |
| 2006/0041181 A1 | 2/2006 | Viswanathan et al. | |
| 2007/0043338 A1 | 2/2007 | Moll et al. | |
| 2007/0083193 A1 | 4/2007 | Werneth et al. | |
| 2007/0103437 A1 | 5/2007 | Rosenberg | |
| 2007/0106247 A1 | 5/2007 | Burnett et al. | |
| 2007/0118079 A1 | 5/2007 | Moberg et al. | |
| 2007/0142749 A1 | 6/2007 | Khatib et al. | |
| 2007/0185486 A1 | 8/2007 | Hauck et al. | |
| 2007/0197896 A1 | 8/2007 | Moll et al. | |
| 2007/0250097 A1 | 10/2007 | Weitzner et al. | |
| 2007/0276216 A1 | 11/2007 | Beyar et al. | |
| 2008/0027313 A1 | 1/2008 | Shachar | |
| 2008/0059598 A1 | 3/2008 | Garibaldi et al. | |
| 2008/0167750 A1 | 7/2008 | Stahler et al. | |
| 2008/0217564 A1 | 9/2008 | Beyar et al. | |
| 2009/0012533 A1 | 1/2009 | Barbagli et al. | |
| 2009/0105639 A1 | 4/2009 | Weitzner et al. | |
| 2009/0110152 A1 | 4/2009 | Manzke et al. | |
| 2009/0131955 A1 | 5/2009 | Wenderow et al. | |
| 2009/0137952 A1 | 5/2009 | Ramamurthy et al. | |
| 2009/0138025 A1 | 5/2009 | Stahler et al. | |
| 2009/0221958 A1 | 9/2009 | Beyar et al. | |
| 2009/0247944 A1 | 10/2009 | Kirschenman et al. | |
| 2010/0069833 A1 | 3/2010 | Wenderow et al. | |
| 2010/0076308 A1 | 3/2010 | Wenderow et al. | |
| 2010/0076309 A1 | 3/2010 | Wenderow et al. | |
| 2010/0076310 A1 | 3/2010 | Wenderow et al. | |
| 2011/0144658 A1 | 6/2011 | Wenderow et al. | |
| 2011/0152882 A1 | 6/2011 | Wenderow et al. | |

FOREIGN PATENT DOCUMENTS

| | | |
|---|---|---|
| EP | 0 554 986 B1 | 8/1993 |
| EP | 0 590 268 B1 | 4/1994 |
| EP | 0 970 663 A1 | 1/2000 |
| EP | 1 415 660 A1 | 5/2004 |
| EP | 1 421 913 A1 | 5/2004 |
| EP | 1 442 720 A1 | 8/2004 |
| EP | 1 504 713 B1 | 7/2008 |
| WO | WO 01/74252 A2 | 10/2001 |
| WO | WO 02/09571 A2 | 2/2002 |
| WO | WO 2006/018841 A3 | 2/2006 |
| WO | WO 2006/120666 A1 | 11/2006 |
| WO | WO 2009/137410 A1 | 11/2009 |
| WO | WO 2010/025336 A1 | 3/2010 |
| WO | WO 2010/025338 A1 | 3/2010 |
| WO | WO 2010/068783 A1 | 6/2010 |
| WO | WO 2010/107916 A1 | 9/2010 |
| WO | WO 2011/046874 A1 | 4/2011 |

OTHER PUBLICATIONS

European Office Action for European Patent Application No. 05764607.7-1265, mailed Jan. 29, 2010, 6 pages.

U.S. Appl. No. 29/378,948, filed Nov. 11, 2010, Murphy.

Beyar et al., Remote-Control Percutaneous Coronary Interventions: Concept, Validation, and First-in-Humans Pilot Clinical Trial, Journal of the American College of Cardiology, Sep. 24, 2005, 5 pages.

* cited by examiner

IMAGE-GUIDED NAVIGATION FOR CATHETER-BASED INTERVENTIONS

CROSS-REFERENCE TO RELATED APPLICATIONS

This application is a National Phase Application of PCT International Application No. PCT/IL2005/000887, entitled "Image-Guided Navigation for Catheter-Based Interventions", International Filing Date Aug. 16, 2005, published on Feb. 23, 2006 as International Publication No. WO 2006/018841, which in turn claims priority from U.S. Provisional Patent Application No. 60/601,629, filed Aug. 16, 2004, both of which are incorporated herein by reference in their entirety.

FIELD OF THE INVENTION

The present invention relates catheter navigation. More particularly it relates to a device and method for navigation of a wire and/or a device within the coronary tree through a combination of a manipulation system and position detection of the wire or device location.

BACKGROUND OF THE INVENTION

Minimally invasive surgery (MIS) is performed through natural body openings or through small surgical incisions. MIS allows access to difficult-to-reach anatomy, minimizes trauma to the patient, and can result in shorter hospital stays and reduced pain. Endoscopic sinus surgery, neurosurgery, spinal surgery, arthroscopic and laparoscopic surgeries are all examples of minimally invasive surgeries.

Image-guided coronary navigation provides the medical practitioner with a visual "roadmap" of the patient's anatomy together with the position of an inserted medical instrument, such as a guidewire, catheter, balloon, stent, or other device.

Currently image-guided coronary navigation is done manually by the practitioner. Using repeated injections of contrast to enable capture of a progression of angiograms, the practitioner navigates a guidewire across the stenosis and then advances a balloon or other device to the treatment site. Roadmaps are difficult to use for cardiology due to the motion of the heart, therefore an overlay of previous injections is not currently used for coronary applications.

The present invention provides a method and system for advancing a guidewire or other device within the coronary tree using a roadmap image (roadmap). Several advantages are thereby obtained, including:

For the patient, there is a marked reduction in the use of contrast agents, thereby preventing renal damage and enhancing the ability to treat patients with multiple lesions in one session. Furthermore, there is a dramatic reduction in the amount of the patient's exposure to x-rays.

For the physician, automated wire positioning enhances his or her ability to treat the disease effectively by faster, more accurate deployment of the guidewire and/or medical device. Furthermore, in cases where the guidewire and/or medical device is positioned with an automatic positioning system, the deployment can be done faster and more accurately and with closed loop control.

Other objects and advantages of the present invention will become apparent after reading the present specification and reviewing the accompanying drawings.

BRIEF DESCRIPTION OF THE INVENTION

There is thus provided, according to some preferred embodiments of the present invention a navigation system for catheter-based interventions, the system comprising:

a processing device;

an angiogram x-ray system connected by data transfer connection to the processing device and capable of capturing angiographic images of a patient;

an electrocardiogram monitoring device that is also connected by data transfer connection to the processing device and to the x-ray system;

a medical instrument to be inserted into the area of the patient captured by the angiographic image;

a position capture module for getting position information about the position of the medical instrument, the unit connected by data transfer connection to the processing device, wherein the processing device is capable of triggering the capturing of the angiographic images as a roadmap and superimposing on the roadmap the position information about the medical instrument.

Furthermore, according to some preferred embodiments of the present invention, the medical instrument is selected from a group comprising: guidewire, balloon, stent and catheter.

Furthermore, according to some preferred embodiments of the present invention, the position capture module is incorporated with the angiogram x-ray system adapted to be triggered periodically by the electrocardiogram monitoring device.

Furthermore, according to some preferred embodiments of the present invention, the position capture module comprises a sensor integrated into the medical instrument and a detector for reading the sensor position.

Furthermore, according to some preferred embodiments of the present invention, the position capture module comprises at least one magnet integrated into the medical instrument and a detector for detecting magnetic field of said at least one magnet.

Furthermore, according to some preferred embodiments of the present invention, the system further comprises a remote manipulation system for performing insertion of the medical instrument, the remote manipulation system comprising:

an attachment unit for attachment to the medical instrument, and a manipulating unit for manipulating the medical instrument.

Furthermore, according to some preferred embodiments of the present invention the remote manipulation system operates in a closed loop, the remote manipulation system further comprising:

a desired position module for receiving a path to a desired target position from a user, a comparator module that compares the actual position of the medical instrument with the desired path position, and a correction module for correcting the medical instrument position.

Furthermore, according to some preferred embodiments of the present invention, there is provided a navigation method for catheter-based interventions, the method comprising:

selecting an angiographic x-ray image, wherein a lesion is most apparent, to serve as a roadmap image, inserting a medical instrument into an artery leading to the lesion, capturing progress of the medical instrument by retrieving angiographic x-ray images, displaying the captured progress of the medical instrument superimposed on the roadmap image, and manipulating the instrument according to the captured progress to reach the target lesion.

Furthermore, according to some preferred embodiments of the present invention, capturing progress of the medical instrument by retrieving angiographic x-ray images is done occasionally.

Furthermore, according to some preferred embodiments of the present invention, capturing progress of the medical instrument by retrieving angiographic x-ray images is done periodically.

Furthermore, according to some preferred embodiments of the present invention, the period is chosen to be the diastole.

Furthermore, according to some preferred embodiments of the present invention, the inserting of the instrument is done using a remote manipulation system.

Furthermore, according to some preferred embodiments of the present invention, the road map is updated occasionally.

Furthermore, according to some preferred embodiments of the present invention there is provided an automated navigation method for catheter-based interventions, the method comprising:

selecting an angiographic x-ray image, wherein a lesion is most apparent, to serve as a roadmap image, tracing a desired path to the lesion, inserting a medical instrument into an artery leading to the lesion, capturing progress of the medical instrument by retrieving angiographic x-ray images comparing the captured position of the instrument with a desired position along the desired path and determining an error if it exists;

if the error is greater than a predefined threshold, correcting the instrument position;

continuing with comparing and correcting until the instrument reaches a desired position.

Furthermore, according to some preferred embodiments of the present invention, the method further comprises manipulating the instrument to overcome an obstacle further by:

detecting the direction of the instrument, determining an optimal degree of rotation for the instrument to overcome the obstacle, and rotating the instrument at the determined optimal degree of rotation.

BRIEF DESCRIPTION OF THE FIGURES

The invention is described herein, by way of example only, with reference to the accompanying Figures, in which like components are designated by like reference numerals.

DETAILED DESCRIPTION OF THE INVENTION

The present invention provides a method and system for advancing a guidewire or other device within the coronary tree using a roadmap image (roadmap).

Figure 1:
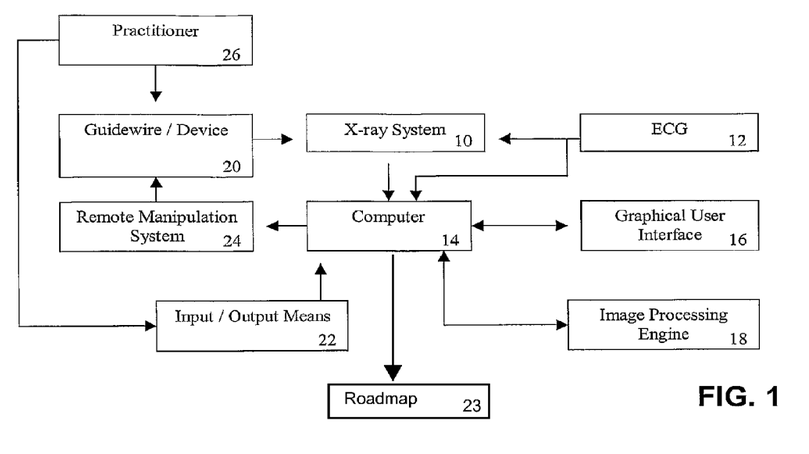
FIG. 1 is a block diagram of a system for image-guided navigation in accordance with a preferred embodiment of the present invention.

For purposes of explanation, this detailed description refers generally to a guidewire 20, however the inserted instrument could equally be another device, such as a stent delivery system, other medical-device delivery system, or catheter. For example, the present invention can be used to navigate a guidewire across a lesion and then to advance a stent (or other device) to the lesion. Navigation can be done manually, semi-automatically, or fully automatically.

The components of the present invention include instruments commonly found in catheter labs with the addition of an image processor and image overlay system. FIG. 1 illustrates a preferred embodiment of the present invention. Angiogram x-ray system 10 obtains images of the cardiac system and can be operated directly by a practitioner 26 or triggered by image processing computer 14 to which it is connected by data connection. Image processing computer 14 is also connected by data connection to electrocardiogram (ECG) 12, which records the electrical activity of the cardiac cycle.

Image processing computer 14 can be configured by an interface, such as graphical-user interface 16, to trigger angiogram acquisition by x-ray 10 at a predefined point in the cardiac cycle. Preferably the trigger point is the end of diastole (ED) as indicated by the R wave input from ECG 12.

Examples of an image processing computers 14 are the CardiOp-B Navigation System, manufactured by Paleon Inc., of New York, N.Y., and the CARTO™ XP EP Navigation and Ablation System manufactured by Biosense Webster Inc. of Diamond Bar, Calif.

Image processing computer 14 also comprises image processing engine 18, which adapts image processing computer 14 to build a roadmap 23 from at least one angiogram and to superimpose on the roadmap the progress of a guidewire 20 or other device as detected over time by angiogram x ray system 10 or by another sensing or imaging system, thereby indicating the position of guidewire 20.

Image processing computer 14 also includes user input/output means 22, such as a keyboard, mouse, joystick and/or touch screen for input and a display (typically the touch screen) for output.

Positioning of guidewire 20 can be done manually or using a remote manipulation system (RMS) 24. The RMS operation can be semiautomatic (where there is no control loop and therefore the practitioner controls navigation) or fully automatic (where there is a control loop and therefore the system automatically corrects navigation errors). A semiautomatic RMS is described in U.S. Pat. No. 6,726,675 to Beyar, incorporated herein by reference, and comprises an attachment unit for attaching the RMS to the guidewire and a manipulating unit for manipulating the guidewire.

An automated RMS further comprises a desired position definition component for setting the desired path for the guidewire (for example, a touch screen on which the practitioner can trace the path and touch screen-input software for converting the trace to coordinates for the control software) and a control component for comparing guidewire position feedback with the defined desired path and correcting the positioning component accordingly.

Figure 2:
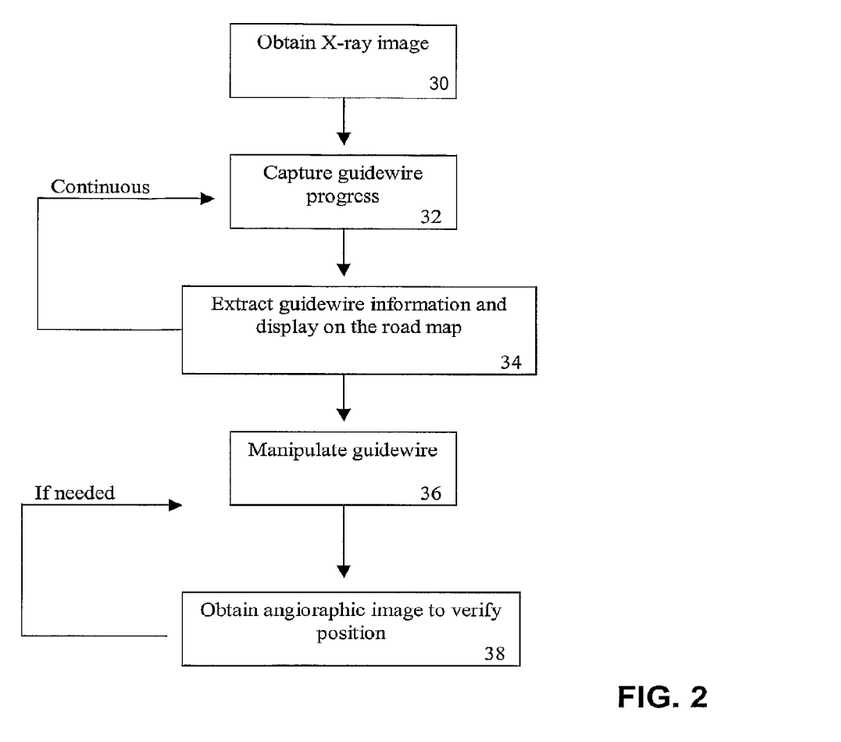
FIG. 2 is a flow chart of a method for image-guided navigation in accordance with a preferred embodiment of the present invention.

With reference to FIG. 2, a method for image-guided navigation for catheter-based interventions in accordance with a preferred embodiment of the present invention is now described. The method is described with reference to guidewire and applies as well for insertion of other medical instruments, such as a stent or balloon.

Step 30: Select an image, wherein the lesion is most apparent, to serve as a roadmap for navigational purposes. Preferably the image is an angiogram taken at the end of diastole (ED) as indicated by the R wave input from ECG 12.

Step 32: Capture the progress of the guidewire insertion using angiograms or other imaging or motion tracking systems, such as a position sensor on the wire (for example, a magnetic detection probe as disclosed in U.S. Pat. No. 6,233,476 to Strommer, et al.). The guidewire is preferably composed of material suited for good reception by the imaging or detection system, for example, a radio-opaque guidewire is well suited for detection by X-ray fluoroscopy. The guidewire-progress capture is preferably done at the same point in the cardiac cycle as when the roadmap image was captured. Preferably, this point in the cycle is the ED.

Step 34: Extract the guidewire-progress information and display it relative to the roadmap image, such that the position change of the wire is shown superimposed over its relative location in the roadmap image.

Preferably the roadmap image is an ED angiogram, on which progressive ED angiograms of the guidewire progress are displayed.

The type of guidewire progress image and the frequency with which it is updated can vary according to the needs of a particular application. Two variations are now described:

In a preferred embodiment of the present invention, an ED angiogram of the guidewire progress is updated on every R wave of the ECG and superimposed on the roadmap image, thereby providing a single guidewire-position update per cardiac cycle. An advantage of this embodiment is that only one ED angiogram is taken every cycle. Therefore the patient is exposed to minimal radiation since ECG-triggered X ray acquisition results in markedly reduced X-ray exposure.

In another preferred embodiment of the present invention, entire loop views from one ED to the next ED, representing a full cardiac cycle, are displayed in real-time on the roadmap image. The wire is displayed on the roadmap image for synchronization between the looped image and the real time guidewire position. An advantage of this embodiment is that the operator views an animated image of the guidewire progress.

Repeat steps 32 and 34 continuously during the procedure to update the wire position on the roadmap.

Step 36: Manipulate the guidewire using manual positioning or using an RMS in semiautomatic or fully automatic operation mode.

Step 38: Optionally take and analyze one or more additional angiograms to verify that the position is correct. Repeat steps 36 and 38 till the guidewire is in the desired location.

Figure 3:
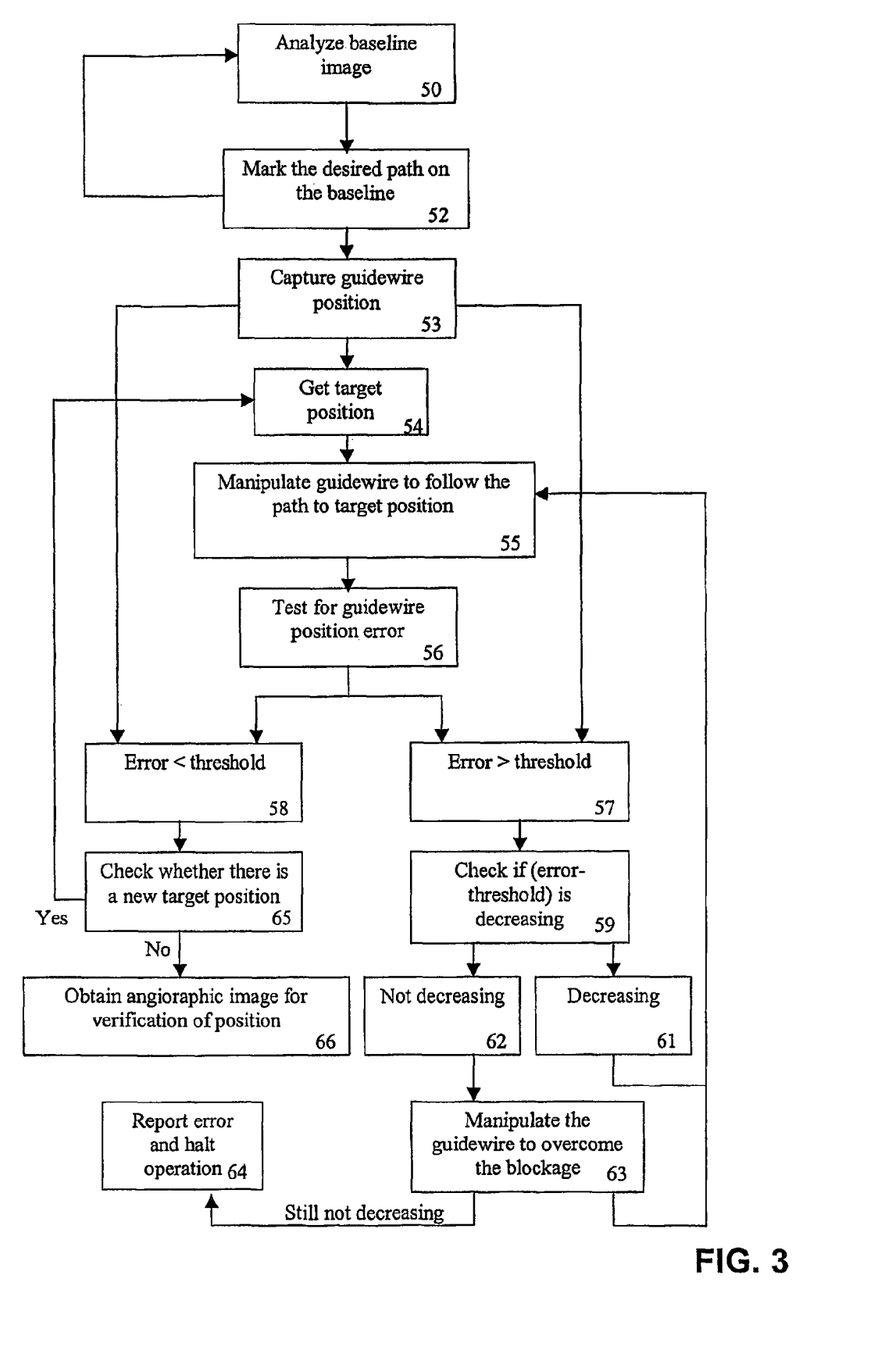
FIG. 3 is a flow chart of a method for employing an automatic positioning system in accordance with a preferred embodiment of the present invention.

A method for automated operation of an automated RMS in accordance with a preferred embodiment of the present invention is now described with reference to FIG. 3.

Step 50: Analyze the image, determining major bifurcation points.

Step 52: Mark the desired path of the wire on the roadmap.

Step 53: Capture guidewire position using image analysis or other position capture.

Step 54: Get a target position from the system. The target is the next position for the guidewire to reach on the path.

Step 54: Advance the guidewire towards the target position while monitoring the guidewire's actual position.

Step 56: Test for error between the actual guidewire position and the target position defined in step 54.

Step 57: If the error of step 56 is greater than a threshold (for example the guidewire has taken a wrong branch), proceed to step 59, otherwise proceed to step 58.

Step 58: If the error of step 56 is less than the threshold, proceed to step 65.

Step 59: Check if the error is decreasing.

Step 61: If the error is decreasing, go to step 54, otherwise

Step 62: If the error is not decreasing, proceed to step 63.

Step 63: Attempt to correct for the blockage that is causing the error to exceed the threshold. An example of a correction is withdrawing the guidewire an appropriate margin, rotating the guidewire to point its tip in the desired direction, and then attempting to advance again. An optional additional step would be to first extract the tip direction from the guidewire image and based on that determine how much to rotate the guidewire to obtain the best new direction for to the tips relative to the roadmap.

Step 64: If step 63 did not solve the problem, there is a mechanical problem or some form of resistance: Halt wire progress and report an error. Resistance can be further verified using techniques known in the art, including force feedback, detection of guidewire buckling, or detection of guidewire being pushed back.

Step 65: Check with the system whether there remain more position targets. (The target is the next position for the guidewire to reach on the path.)

If there are any targets remaining, it means that the guidewire has not yet reached its final target. Therefore, go to step 54 to get the next position target.

If there are no targets remaining, it means that the guidewire has reached its final position. Therefore, proceed to step 66.

Step 66: Acquire a new angiographic image to verify that the guidewire has reached its final target destination (end of path).

In a preferred embodiment of the present invention, once the guidewire has been positioned in place, a medical device 21, such as a stent or balloon, can be automatically advanced over the guidewire using a similar procedure until it reaches the desired location.

A number of alternative configurations are possible for the present invention regarding identifying the position of, and manipulating, guidewire 20 and/or medical device 21:

The image can be 2D or 3D.

Position feedback can be received from a positioning signal (for example, RF, magnetic, or MRI) generated by guidewire 20 and/or medical device 21, to help in detecting its position. An example of such an implementation is the Carto EP Navigation System, manufactured by Blosense Webster Inc. of Diamond Bar, Calif. Another example is a GStent system manufactured by MediGuide Ltd. of Haifa, Israel.

The RMS could be one of various systems, such as the following:

U.S. Pat. No. 6,834,201 to Glilies, et al., describes a method of magnetically manipulating a medical device within a body part of a human patient in conjunction with MR imaging including applying a navigating magnetic field with magnets from the MR imaging device, and changing the magnetic moment of the medical device to change the orientation of the medical device within the body part.

U.S. Pat. No. 5,654,864 describes a control method for magnetic stereotaxis system. A control method permits the operation of multiple superconducting magnetic coils so as to move a magnetic object to precisely specified locations within the body under command of a physician-operator observing the motion with live fluoroscopic imaging fused with more detailed preoperative imaging of some other kind. A computer contains the preoperative images and the fluoroscopic images, as well as the means to effect changes in the coil currents so as to accomplish the desired magnetic object motion and positioning. The control method operates the coils in pairs on opposite sides of the body in a manner to minimize the necessary current changes, thus avoiding the quenching of the superconducting coils. Combinations of these pairs can execute motion of the magnetic object in any direction in an impulsive manner and with high precision. The method should function well and provide advantages with coils which are not superconducting as well. The method overcomes the redundance present in the limited constraints given by a simple movement vector by the physician-operator In addition to the main uses for the present invention outlined earlier, the invention can be integrated into other medical applications that benefit from the improved positioning provided by the present invention. The following are examples of applications that could benefit from integration with the present invention:

An application to make a 3D reconstruction (map) of the heart, thereby mapping the heart. An application of this patent is ability to show and point the exact positioning of the device.

An application to find the positioning of a device using a magnetic sensor.

Stereotaxis: an application wherein a device is navigated within a magnetic field.

U.S. Patent application 20050008210 described a system and method for three-dimensional reconstruction of an artery. A method and system for imaging an artery contained in an arterial tree. A microprocessor generates a three-dimensional reconstruction of the arterial tree from two or more angiographic images obtained from different perspectives. The orientation of the axis of the artery in the arterial tree is then determined, and a perspective of the artery perpendicular to the axis of the artery is determined. A three dimensional reconstruction of the artery from angiographic images obtained from the determined perspective is then generated.

U.S. Pat. No. 6,233,476 described a medical positioning system medial device comprising a housing, a magnetic detection probe, for detecting a plurality of magnetic fields, a biometric unit and a controller, connected to said magnetic detection probe, said biometric unit and said storage unit, wherein said controller receives magnetic field detection information from said magnetic detection probe, and wherein said controller operates said biometric unit in association with said magnetic field detection information.

It should be clear that the description of the embodiments and attached Figures set forth in this specification serves only for a better understanding of the invention, without limiting its scope as covered by the following claims.

It should also be clear that a person skilled in the art, after reading the present specification could make adjustments or amendments to the attached Figures and above described embodiments that would still be covered by the following claims.

The invention claimed is:

1. A navigation system for inserting a medical instrument in a patient, the system comprising:
   a medical instrument;
   a processing device;
   an angiogram x-ray system in communication with the processing device and capable of capturing a series of angiographic images of the patient during the insertion of the medical instrument in the patient wherein at least one of the angiographic images captures the medical instrument that was inserted into an area of the patient; and
   a position capture module configured to get position information about the position of the medical instrument from angiographic images of the progress of the medical instrument generated by the angiographic x-ray system, the position capture module in communication with the processing device;
   the processing device superimposing the position information about the medical instrument on a roadmap image, wherein the roadmap image is one of the series of angiographic images generated by the angiographic x-ray system, the processing device updating the roadmap occasionally during the insertion of the medical instrument in the patient, the processing device superimposing subsequent angiographic images on the updated roadmap.

2. The system of claim 1 wherein the medical instrument is selected from a group consisting of: a guidewire, a balloon, a stent and a catheter.

3. The system of claim 1 further comprising an electrocardiogram monitoring device in communication with the processing device and the angiogram x-ray system, wherein the position capture module is adapted to be triggered periodically by the electrocardiogram monitoring device.

4. The system of claim 1 further comprising a remote manipulation system configured to perform insertion of the medical instrument, the remote manipulation system comprising:
   an attachment unit configured to attach the medical instrument to the remote manipulation system; and
   a manipulating unit configured to manipulate the medical instrument.

5. The system of claim 4 wherein the remote manipulation system operates in a closed loop, the remote manipulation system further comprising:
   a desired position module that receives a path to a desired target position from a user;
   a comparator module that compares the actual position of the medical instrument with the desired path position; and
   a correction module that corrects the medical instrument position.

6. The system of claim 5 further comprising a touch screen, wherein the desired position module receives the path from the user via the touch screen.

7. The system of claim 1 wherein the position capture module is configured to get the position information of the medical instrument via image analysis of the angiographic images of the progress of the medical instrument.

8. The system of claim 1 wherein the angiographic images of the progress of the medical instrument are captured at the same point in the cardiac cycle as the roadmap image.

9. The system of claim 8 wherein the roadmap image is an angiographic image captured at the end of diastole and further wherein the angiographic images of the progress of the medical instrument are also captured at the end of diastole.

10. A navigation method for inserting a medical instrument in a patient, the method comprising:
   selecting an angiographic x-ray image including a lesion to serve as a roadmap image, wherein the roadmap image is generated using an angiogram x-ray system;
   inserting a medical instrument into an artery leading to the lesion;
   capturing progress of the medical instrument from angiographic x-ray images of the progress of the medical instrument, wherein the angiographic x-ray images of the progress of the medical instrument are generated using the angiogram x-ray system;
   displaying the captured progress of the medical instrument superimposed on the roadmap image;

updating the roadmap image from angiographic images generated during the insertion of the medical instrument in the patient;

capturing subsequent progress of the medical instrument from angiographic x-ray images of the progress of the medical instrument, updating the position of the medical instrument on the updated roadmap displaying the captured progress of the medical instrument superimposed on the updated roadmap image; and manipulating the instrument to reach the lesion.

11. The method of claim 10 wherein capturing progress of the medical instrument is done occasionally.

12. The method of claim 10 wherein capturing progress of the medical instrument is done periodically.

13. The method of claim 10 wherein capturing progress of the medical instrument occurs during each period of diastole.

14. The method of claim 10 wherein the inserting of the instrument is done using a remote manipulation system.

15. The method of claim 10, wherein updating the roadmap image from angiographic images generated during the insertion of the medical instrument in the patient is done occasionally.

16. An automated navigation method for inserting a medical instrument in a patient, the method comprising:

selecting an angiographic x-ray image showing a lesion to serve as a roadmap image, wherein the roadmap image is generated using an angiogram x-ray system during insertion of a medical instrument in a patient;

tracing a desired path to the lesion;

inserting the medical instrument into an artery leading to the lesion using a remote manipulation system;

capturing progress of the medical instrument from angiographic x-ray images of the progress of the medical instrument;

comparing the captured position of the instrument with a desired position along the desired path and determining an error if it exists;

correcting the instrument position if the error is greater than a predefined threshold;

updating the roadmap image with an angiographic image generated by the angiographic x-ray system during inserting of the medical instrument in the patient; and continuing with comparing and correcting until the instrument reaches a desired position.

17. The method of claim 16 further comprising manipulating the instrument to overcome an obstacle by:

detecting the direction of the instrument;

determining an optimal degree of rotation for the instrument to overcome the obstacle; and rotating the instrument at the determined optimal degree of rotation.

18. The method of claim 16 wherein the step of tracing a desired path includes tracing the desired path on a touch screen.

* * * * *

UNITED STATES PATENT AND TRADEMARK OFFICE
CERTIFICATE OF CORRECTION

PATENT NO. : 8,600,477 B2
APPLICATION NO. : 11/660320
DATED : December 3, 2013
INVENTOR(S) : Rafael Beyar and Tal Wenderow

It is certified that error appears in the above-identified patent and that said Letters Patent is hereby corrected as shown below:

On the title page, Item (73) Assignee "Corinduc, Inc."

Should read:

"Corindus, Inc."

Signed and Sealed this
Twenty-ninth Day of April, 2014

Michelle K. Lee
*Deputy Director of the United States Patent and Trademark Office*